(12) United States Patent
Haley (10) Patent No.: US 12,083,235 B2
(45) Date of Patent: Sep. 10, 2024

(54) SANITIZING WEIGHTED BRACELET

(71) Applicant: Better Way Inventions LLC, Boca Raton, FL (US)

(72) Inventor: Stephen Haley, Boca Raton, FL (US)

(73) Assignee: Better Way Inventions LLC, Boca Raton, FL (US)

( * ) Notice: Subject to any disclaimer, the term of this patent is extended or adjusted under 35 U.S.C. 154(b) by 366 days.

(21) Appl. No.: 17/689,953

(22) Filed: Mar. 8, 2022

(65) Prior Publication Data
US 2022/0280664 A1 Sep. 8, 2022

Related U.S. Application Data

(60) Provisional application No. 63/157,937, filed on Mar. 8, 2021.

(51) Int. Cl.
| | |
|---|---|
| *A61L 2/00* | (2006.01) |
| *A61L 2/26* | (2006.01) |
| *A63B 21/00* | (2006.01) |
| *A63B 21/065* | (2006.01) |

(52) U.S. Cl.
CPC ............ *A61L 2/0088* (2013.01); *A61L 2/26* (2013.01); *A63B 21/065* (2013.01); *A63B 21/4021* (2015.10); *A61L 2202/121* (2013.01); *A61L 2202/15* (2013.01); *A61L 2202/16* (2013.01)

(58) Field of Classification Search
CPC .......................... A61L 2/0088; A63B 21/4021
USPC ........................................................ 222/175
See application file for complete search history.

(56) References Cited

U.S. PATENT DOCUMENTS

| | | | | |
|---|---|---|---|---|
| 5,957,347 | A | * | 9/1999 | White ............... A63B 21/0602 224/148.1 |
| 6,126,041 | A | * | 10/2000 | DiTomasso .......... A63B 21/065 224/148.1 |
| 7,316,332 | B2 | * | 1/2008 | Powers ............... A61M 35/003 222/491 |
| 11,700,920 | B2 | * | 7/2023 | Chacon, Jr. .......... A47K 5/1202 222/175 |
| 2013/0237391 | A1 | * | 9/2013 | Haley .............. A63B 21/00065 482/105 |
| 2016/0129296 | A1 | * | 5/2016 | Haley .................. A63B 21/065 482/105 |

(Continued)

*Primary Examiner* — Jeremy Carroll
(74) *Attorney, Agent, or Firm* — Johnson | Dalal; Mark C. Johnson (57) ABSTRACT

A sanitizing weighted bracelet with a strap body operably configured to define an enclosure to surround a user's limb, at least one raised section operably configured to house and retain at least one metallic weight, and a sanitizing raised section an upper surface at least partially defining an upper surface of the strap body and defining an access aperture, with a front surface defining an aperture, with a rear surface, and defining at least one channel spatially connected to the access aperture and the aperture defined by the front surface of the sanitizing raised section. The sanitizing raised section also includes a flexible sanitizing container disposed therein and that includes a nozzle projecting outwardly from the aperture of the sanitizing raised section. The flexible sanitizing container is operably configured to be accessible through the access aperture and flexed to cause emission of a sanitizing liquid from a nozzle thereon.

17 Claims, 5 Drawing Sheets

(56) References Cited

U.S. PATENT DOCUMENTS

2021/0353788 A1\* 11/2021 Crawford .............. B05B 11/026
2021/0393814 A1\* 12/2021 Klepfisz ................ A61L 2/0088

\* cited by examiner

FIG. 5

SANITIZING WEIGHTED BRACELET

FIELD OF THE INVENTION

The present invention relates generally to wearable sanitizing assemblies and, more particularly, relates to a weighted bracelet operably configured to store and dispense a sanitizing or disinfectant medium.

BACKGROUND OF THE INVENTION

Many people throughout the world exercise with a variety of different tools configured to enhance the exercise routine of those individuals or "users" of said tools. Many users utilize a weighted bracelet to facilitate in exercising, which has significant health and cardiovascular benefits. Many users, however, desire a quick and effective way to sanitize or disinfect their hands while exercising. Those known weighted bracelets fails to enable users to accomplish the same in a safe, effective, and efficient manner.

Therefore, a need exists to overcome the problems with the prior art as discussed above.

SUMMARY OF THE INVENTION

The invention provides a sanitizing weighted bracelet that overcomes the hereinafore-mentioned disadvantages of the heretofore-known devices and methods of this general type and that enables a user to exercise with the weighted bracelet while simultaneously being able to transport and emit a sanitizing or disinfectant therefrom. As such, users are able to utilize a weighted bracelet in a healthy and safe manner with the sanitizer quickly accessible for emission, e.g., utilizing a pump housed within one of the sections of the weighted bracelet and with a nozzle angled toward the user's body.

With the foregoing and other objects in view, there is provided, in accordance with the invention, a sanitizing weighted bracelet having a strap body operably configured to define an enclosure to surround a user's limb, defining a longitudinal strap length, having an upper surface, and having a bottom surface opposing the upper surface of the strap body. The bracelet also includes at least one raised section disposed transversely along the strap length, at least partially defining the upper surface of the strap body, with a front surface, with a rear surface opposing the front surface of the at least one raised section, defining at least one channel spanning in a transverse direction and with at least one metallic weight disposed and retained therein, and defining an aperture spatially coupled to the at least one channel, wherein the at least one metallic weight is operably configured to be selectively and removably retained within the at least one channel of the at least one raised section. Further, the bracelet also includes a sanitizing raised section disposed transversely along the strap length, with an upper surface at least partially defining the upper surface of the strap body and defining an access aperture, with a front surface defining an aperture, with a rear surface opposing the front surface of the sanitizing raised section, and defining at least one channel spanning in a transverse direction and spatially connected to the access aperture and the aperture defined by front surface of the sanitizing raised section. Beneficially, the bracelet includes a flexible sanitizing container disposed within the at least one channel defined by the sanitizing raised section and including a nozzle projecting outwardly from the aperture defined by front surface of the sanitizing raised section, the flexible sanitizing container operably configured to be accessible through the access aperture and flexed to cause emission of a sanitizing liquid configured to be housed in the flexible sanitizing container through the nozzle.

In accordance with another feature, an embodiment of the present invention includes a housing structure of a substantially rigid material, disposed within the at least one channel defined by the sanitizing raised section, defining a housing cavity with the flexible sanitizing container disposed therein, having an upper housing surface defining a depression aperture spatially coupled to and disposed in an overlapping configuration with the access aperture, wherein the flexible sanitizing container is operably configured to be accessible through the access aperture and the depression aperture.

In accordance with a further feature of the present invention, the access aperture is enclosed by the upper surface of the sanitizing raised section and the depression aperture is enclosed by the upper housing surface of the housing structure.

In accordance with an additional feature, an embodiment of the present invention also includes the housing structure having a front surface defining a housing side aperture thereon and a rear surface opposing the front surface of the housing structure, wherein the housing side aperture is spatially coupled to and disposed in an overlapping configuration with the aperture defined by the front surface of the sanitizing raised section and with the nozzle projecting outwardly therefrom.

In accordance with a further feature, an embodiment of the present invention also includes the housing structure having an upper shell and a lower shell selectively removably coupled together to collectively define the housing side aperture.

In accordance with a further feature of the present invention, the housing structure is compressively retained by the sanitizing raised section.

In accordance with an additional feature, an embodiment of the present invention also includes a one-way valve fluidly coupled to the flexible sanitizing container and the nozzle and operably configured to limit emission of the sanitizing liquid configured to be housed in the flexible sanitizing container in one direction through the nozzle.

In accordance with an exemplary feature of the present invention, the raised section is disposed adjacent to the at least one raised section.

In accordance with a further feature, an embodiment of the present invention also includes a plurality of raised sections each disposed transversely along the strap length and each defining at least one channel spanning in a transverse direction and with at least one metallic weight disposed and retained therein, the raised section is disposed adjacent to at least one of the plurality of raised sections.

In accordance with yet another feature, an embodiment of the present invention also includes each of the plurality of raised sections have a top surface at least partially defining the upper surface of the strap body, at least one perpendicular sidewall extending in a direction substantially perpendicular to the top surface, a front surface defining a front face aperture, a rear surface opposing the front surface, and a section width separating the rear surface and the front surface and a discontinuous upper slit defined by the at least one perpendicular sidewall of each of the plurality of raised sections flanking the upper slit, wherein the upper slit spans the section width of each the plurality raised sections defining the upper slit and terminating into a valley that at least partially defines the upper surface of the strap body.

In accordance with another feature of the present invention, the aperture defined by the at least one raised section is defined by the front surface thereon, the at least one raised section defining two independent channels therein, spanning in a transverse direction, and with a metallic weight disposed and retained therein, each of the apertures defined by the front surface of the at least one raised section providing access to the two independent channels.

In accordance with yet another feature of the present invention, the nozzle defines a distal tip defining an aperture offset a distance from the front surface of the sanitizing raised section and oriented at an acute angle α relative to a plane defined by the front surface of the sanitizing raised section.

In accordance with yet another feature, an embodiment of the present invention also includes a fastener disposed proximal to a first end defined by the strap body and a retention portion spanning from a second end defined by the strap body, terminating along a strap length separating the first and second ends of the strap body, and defining a plurality of retention apertures thereon, the fastener operably configured to be inserted through one of the plurality of retention apertures to form an enclosed and locked strap configured to surround the user's limb.

Although the invention is illustrated and described herein as embodied in a sanitizing weighted bracelet, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. More specifically, the inventive strap may be advantageously employed with a variably weighted strap assembly having components and features described in U.S. Pat. Nos. 9,302,141, 9,707,431, 9,604,091 (all issued to Applicant) (the entirety of which are incorporated herein by reference). The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the user's perspective of the device. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the strap, spanning from one end to another end, or in the direction that encloses or surrounds a user's limb. The "transverse" should be understood to mean a direction corresponding opposite to the longitudinal direction or from the front surface to the rear surface of the strap.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION OF INVENTION

The invention described herein provides a sanitizing weighted bracelet that overcomes known disadvantages of those known devices and methods of this general type and that enables a user to participate in weighted exercise or conditioning in a safe and effective manner that permits the user to efficiently and effectively sanitize a user's hand(s) or other surfaces using a flexible container configured to house a sanitizing or other solution/liquid and emit the same therefrom.

Figure 1:
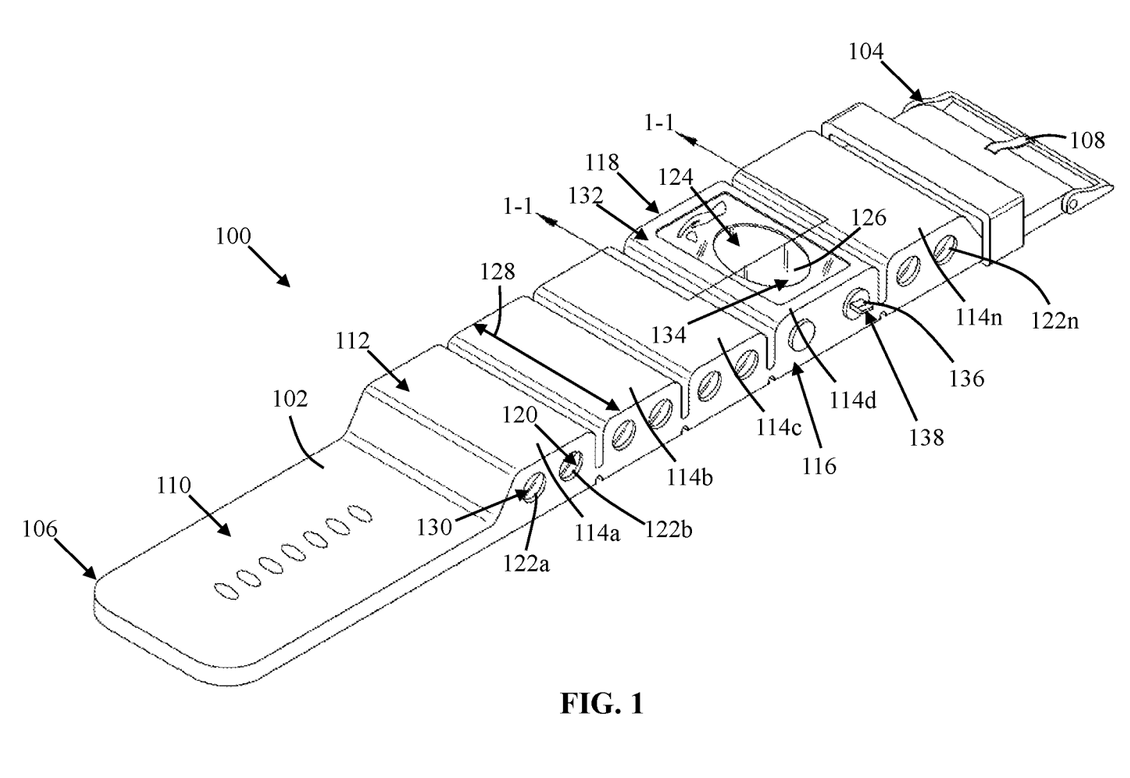
FIG. 1 is a perspective view of a sanitizing weighted bracelet in accordance with one embodiment of the present invention.
Figure 2:
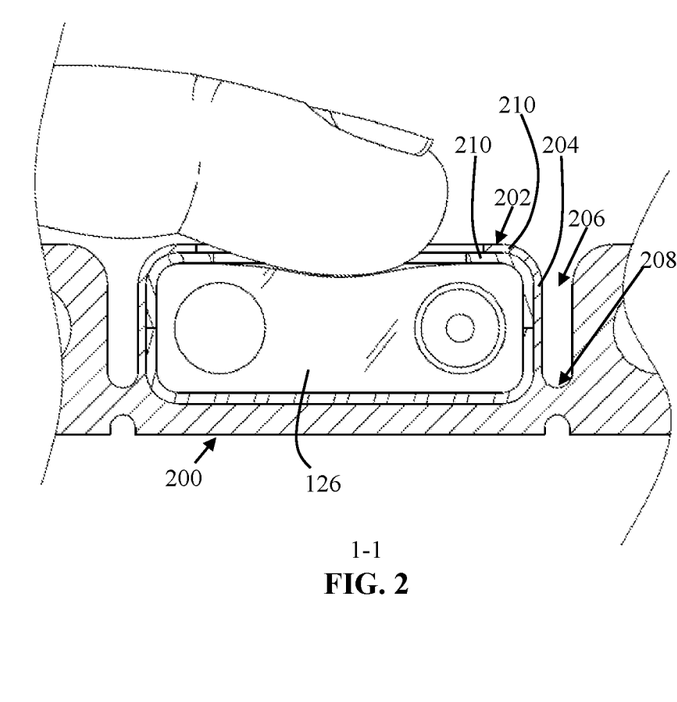
FIG. 2 is a cross-sectional view along section line 1-1 depicting a user depressing a flexible sanitizing container housed within a housing structure in accordance with one embodiment of the present invention.
Figure 3:
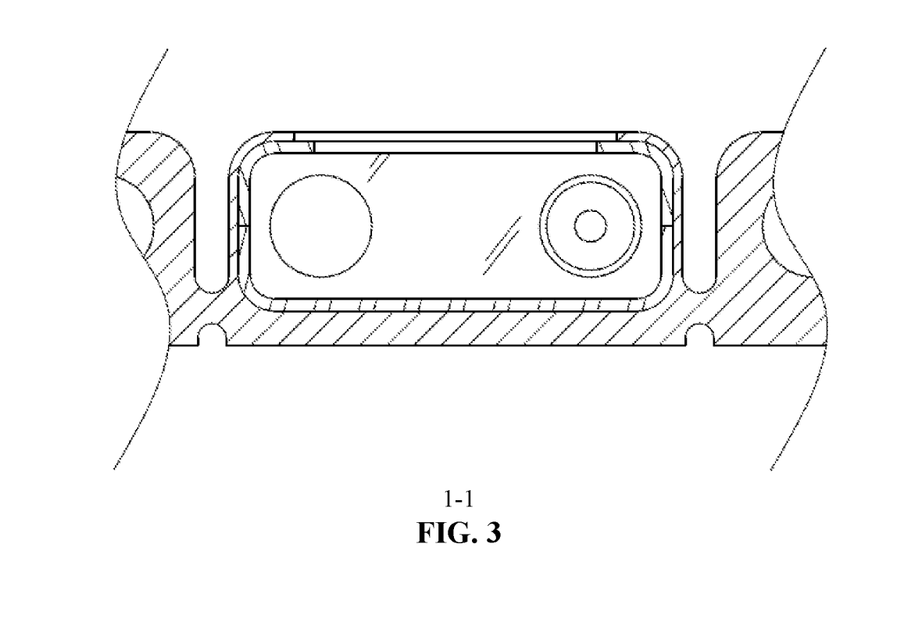
FIG. 3 is a cross-sectional view along section line 1-1 depicting the flexible sanitizing container housed within the housing structure not depressed by a user in accordance with one embodiment of the present invention.
Figure 4:
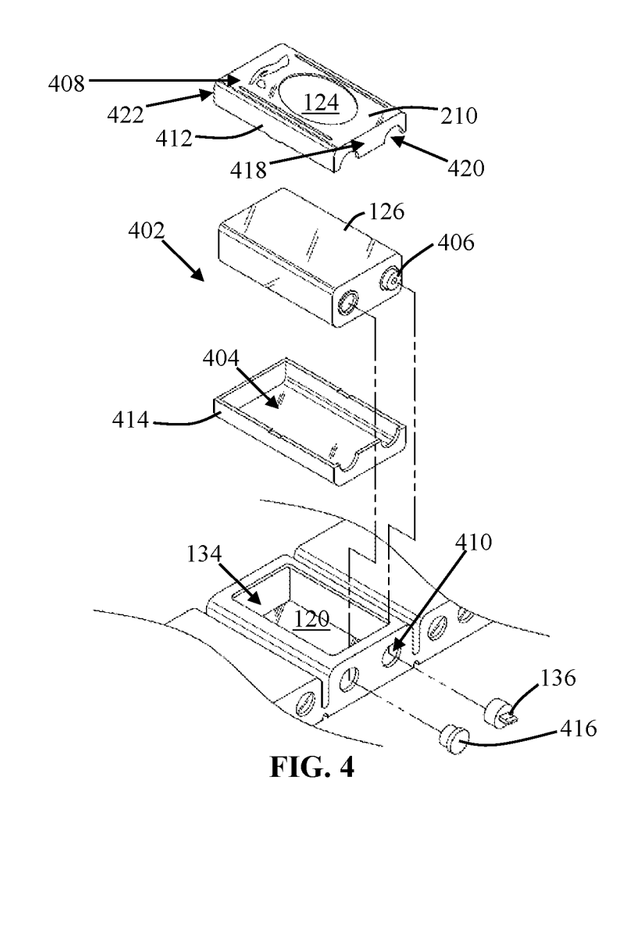
FIG. 4 is a fragmentary exploded view of the flexible sanitizing container housed within the housing structure in accordance with one embodiment of the present invention.
Figure 5:
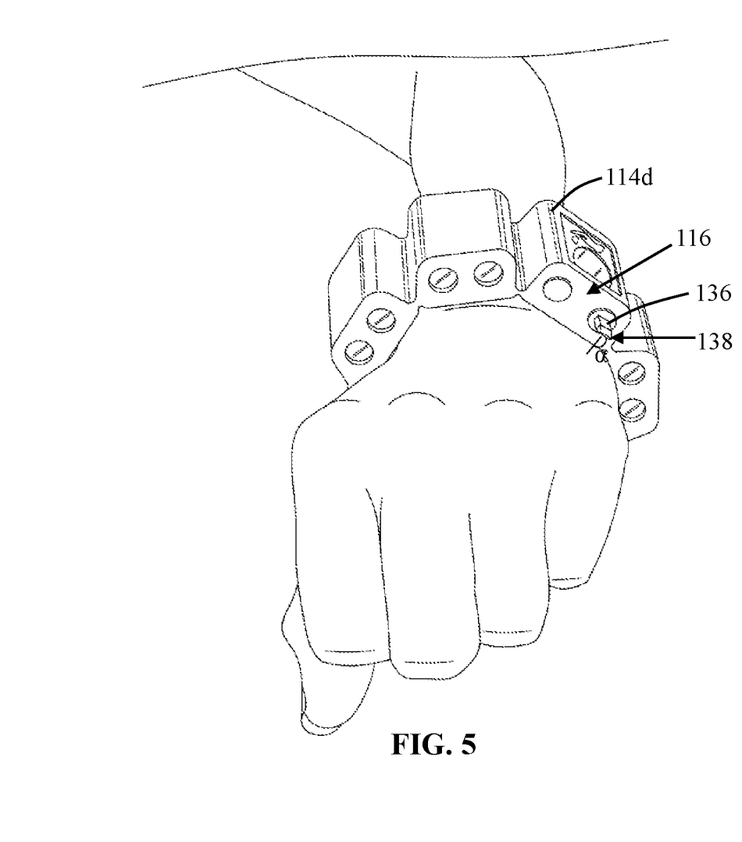
FIG. 5 is a perspective view of the sanitizing weighted bracelet surrounding a user's limb in accordance with one embodiment of the present invention.

Referring now to FIGS. 1-5, one embodiment of the present invention is shown in various views. FIGS. 1-5 show several advantageous features of the present invention, but, as will be described below, the invention can be provided in several shapes, sizes, combinations of features and components, and varying numbers and functions of the components. The first example of a sanitizing weighted bracelet 100, as shown in FIGS. 1-2, includes a strap body 102 with a first end 104, a second end 106 opposing the first end 104 of the strap body 102, a strap length separating the first and second ends 102, 104, an upper surface 112 and a bottom surface 200, opposing the upper surface 112, that span the strap length. The strap body 102 is operably configured to surround a user's limb, e.g., wrist (as shown in FIG. 5), leg, etc. The strap body 102 may include two free ends as shown in the figures, or may be of a continuous circular structure that is operably configured to expand and flex and placed around a user's limb. To that end, the strap body 102 may be of a deformable and flexible polymeric material, such as natural rubber or neoprene. The strap body 102 may also be described as being operably configured to define an enclosure to surround a user's limb (exemplified in FIG. 5), defining a longitudinal strap length (best seen in FIG. 1), having an upper surface 112, and having a bottom surface 200 opposing the upper surface 112 of the strap body. The longitudinal strap length may also define the circumference of the strap body 102 when enclosing the user's limb (which may or may not include fasteners, e.g., like the buckle 108, attached thereto that are configured to attach to a series of apertures on a coupling portion of the strap body 102).

The strap body 102 be seen having a plurality of generally rectangular or raised sections 114a-n, wherein "n" represents any number greater than one. The generally rectangular sections 114a-n may be of another shape and may be disposed transversely along the strap length. The generally rectangular sections 114a-n may also include a top surface 202 at least partially defining the upper surface 112 of the strap body 102, at least one (but in some instances two) perpendicular sidewall 204 extending in a direction substantially perpendicular to the top surface 202, a front surface 116 defining a front face aperture (e.g., apertures 130, 410), a rear surface 118 opposing the front surface, and a section width (e.g., section width 128) separating the rear surface 118 and the front surface 116. The front and rear surfaces 116, 118 can be seen flanking and disposed at substantially perpendicular angles with respect to the upper surface 112 of the strap body 102, thereby enabling the plurality of weights 122a-n to be offset from the user's limb and properly angling and/or offsetting the nozzle of the 408 of a flexible sanitizing container 126 from target area and/or user's limb. Each of the generally rectangular sections 114a-n have a discontinuous upper slit 206 defined by one or two perpendicular sidewall(s) 204 of one or more of the plurality of generally rectangular sections 114a-n flanking the upper slit 206. Specifically, the upper slit 206 spans the section width of each the plurality generally rectangular sections 114a-n defining the upper slit 206 and terminates into a valley 208 that at least partially defines the upper surface 116 of the strap body 102. In one embodiment, the aperture 130 defined by the at least one raised section 114a-n is defined by the front surface 116 thereon and includes another aperture proximal thereto (i.e., adjacent, or near—within 0.5 inches). Each of the apertures defined by the front surface 116 provide access to two independent channels defined within the at least one raised section 114a-n, that also span in a transverse direction, and each have a metallic weight disposed and retained therein.

With reference to FIG. 1 and FIG. 4, the plurality of generally rectangular sections 114a-n also define one or more channel(s) 120 spatially coupled to the front face aperture 410 and spanning transversely along the strap length in direction from the front surface 116 to the rear surface 118 of each of the plurality of generally rectangular sections 114a-n. In one embodiment, each of the plurality of generally rectangular sections 114a-n have two individual channels 120 spatially coupled to two individual front face apertures 410. In other embodiments, a single channel 120 (as shown in FIG. 4) may be utilized. The channels 120 are primarily utilized for housing and retaining one or more weights or pegs 122a-n, but the channel 120 may also be utilized to house and retain (sometimes in a compression or friction-fit configuration because of the flexible material of the strap body 102) a housing structure 402. To that end, one of the plurality of generally rectangular sections 114a-n define an access aperture 134 thereon (that may be enclosed) and is spatially coupled with the channel 120 defined therein. In preferred embodiments, an upper wall 210 of the housing structure 402 defines the access aperture 134 and may also form a perimeter flange that is configured to partially surround and cover the housing structure 402. In other embodiments, a plurality of weights 122a-n may each be selectively and removably retained within each respective channel(s) 120 of one of the respective plurality of generally rectangular sections 114a-n using, for example, friction or compression of the material of the strip body 102 and without the need for any ancillary fasteners.

In one embodiment, the housing structure 402 may be composed of an upper shell 412 that includes the upper wall 210 and a lower shell 414 selectively removably couplable together using, for example, a snap-fit configuration. The housing structure 402 may be of a rectangular shape and disposed within the channel 120 that is spatially coupled with the enclosed access aperture 134. The housing structure 402, specially both shells 412, 414, may partially or completely define and encapsulate a housing cavity 404 and a depression aperture 124 spatially coupled to the housing cavity 404. Further, the upper and lower shells 412, 414 may also selectively removably coupled together to collectively define the housing side aperture 420.

The housing structure 402 may include multiple walls forming the housing cavity 404 (as seen in FIG. 4). In one embodiment, the housing structure 402 includes a front surface 418 defining a housing side aperture 420 thereon and a rear surface 422 opposing the front surface 418 of the housing structure 402, wherein the housing side aperture 420 is spatially coupled to and disposed in an overlapping configuration with the aperture 410 defined by the front surface 116 of the sanitizing raised section 114d and with the nozzle 136 projecting outwardly therefrom, i.e., at least partially disposed in and extending outwardly away from.

The depression aperture 124 may be sized and shaped to receive a user's finger therethrough (as seen in FIG. 2), e.g., approximately 0.5-2 inches in diameter. The housing structure 402 is of a substantially rigid material, such as PVC, stainless steel, aluminum, etc., that is operable to resist plastic or elastic deformation caused by the strap body 102 when the housing structure 402 is disposed therein. To that end, the housing structure 402 is shaped and sized to be received within the at least one channel 120 defined by the sanitizing raised section 114d, i.e., of the same or similar shape and approximately equal to (+/−0.25 inches) or less than. In one embodiment, the elasticity of the strap body 102 beneficially retains the housing structure 402, thereby preventing or inhibiting inadvertent emission of liquid within the flexible sanitizing container 126.

The housing structure 402 has a flexible sanitizing container 126 disposed within the housing cavity 404 for depression by the user through the depression aperture 124, thereby causing emission of a sanitizing solution housed within the flexible sanitizing container 126. The flexible sanitizing container 126 may be of a polymeric material and may be deformably resilient (e.g., PET, PE, HDPE, LDPE, PC, etc.). The flexible sanitizing container 126 may include a one-way or check valve 406 and a nozzle 136 projecting from the front face aperture 410 spatially coupled to the channel 120 spatially coupled with the enclosed access aperture 134. In one embodiment, the nozzle 136 may be rotatably coupled to the valve/port to angle the nozzle 136 to a desired orientation facing the user's hands/palms (best seen in FIG. 5). The one-way valve 406 is fluidly coupled to the flexible sanitizing container 126 and the nozzle 136 and operably configured to limit emission of the sanitizing liquid configured to be housed in the flexible sanitizing container in one direction through the nozzle 136, i.e., in the opposite direction of the target area. In embodiment, best seen in FIG. 5, the nozzle 136 defines a distal tip 138 defining an aperture offset a distance (e.g., 0.25 inches) from the front surface 116 of the sanitizing raised section 114d and oriented at an acute angle α (e.g., 75° relative to a plane defined by the front surface 116 of the sanitizing raised section 114d.

Specifically, the flexible sanitizing container 126 may have one or more ports defined thereon for accessing a container cavity housing the sanitizing or disinfecting liquid or solution. One of the ports may include the check valve 406 coupled in a watertight configuration thereto that is coupled to the nozzle 136. Another port may have a threaded or other configuration operably configured to receive and engage with a cap or cover 416, wherein the removal of the cover 416 provides a user with access to the container cavity. To that end, the flexible sanitizing container 126 may be efficiently and effectively refilled by the user when desired. In one embodiment, the port providing access to the container cavity may be accessible through the front face aperture 410 when the housing 402 is inserted within the channel 120. Specifically, in one embodiment, the sanitizing raised section 114d and flexible sanitizing container 126 (and the housing structure 402 when utilized) include an access port providing selective access for the user to refill the flexible sanitizing container 126, wherein the port may be covered and sealed with a cap 416 when the user does not desire to refill the flexible sanitizing container 126.

The flexible sanitizing container 126 is operably configured to be beneficially accessed and flexed (or depressed—as exemplified in FIG. 2) from the depression aperture 124 to cause emission of a sanitizing liquid housed in the flexible sanitizing container 126 through the one-way valve 406 and the nozzle 136. In one embodiment, the access aperture 134 is enclosed by the upper surface 132 of the sanitizing raised section 114d and the depression aperture 124 is enclosed by the upper housing surface 408 of the housing structure 402. Said structural configuration ensures adequate support and retention of the housing structure 402 when inserted within the channel 120 defined by the sanitizing raised section 114. To that end, the housing structure 402 includes an upper housing surface 408 is directly adjacent to and contacting a lower surface of the upper wall of the strap body 102 for the sanitizing raised section 114d. As best seen in FIGS. 2-3, the depression aperture 124 is spatially coupled to, and disposed in an overlapping configuration with, the access aperture 134, thereby enabling effective and efficient access to the flexible sanitizing container 126.

As seen in FIG. 5, the user places the strap body 100 around the user's limb and fastens it in a retained configuration. The user can then utilize the weighted bracelet for toning and conditioning. When the user desires emission of a sanitizing solution, the user may rotate the weighted bracelet to aim and direct the nozzle 136 toward a user's hands or other target area. The user will then depress the flexible sanitizing container 126 through the access aperture(s) to cause the valve to open allow the transportation and subsequent emission of sanitizing solution through the nozzle 136 and toward the target area. In other embodiments, no valve is utilized, and the external pressure and/or sanitizing viscosity causes the sanitizing liquid to remain within the container cavity. In further embodiments, the flexible sanitizing container 126 may also not include a valve, but may include cover or cap for the nozzle 136. The user would be required to remove the cover or cap for the nozzle 136 and then depress the flexible sanitizing container 126 to cause emission of the sanitizing solution.

Although a specific order of executing steps associated with the use of the sanitizing weighted bracelet 100 has been disclosed, the order of executing the steps may be changed relative to the order shown in certain embodiments. Also, two or more steps shown or described as occurring in succession may be executed concurrently or with partial concurrence in some embodiments. Certain steps may also be omitted for the sake of brevity. In some embodiments, some or all of the process steps can be combined into a single process.

What is claimed is:
1. A sanitizing weighted bracelet comprising:
a strap body operably configured to define an enclosure to surround a user's limb, defining a longitudinal strap length, having an upper surface, and having a bottom surface opposing the upper surface of the strap body;
at least one raised section disposed transversely along the strap length, at least partially defining the upper surface of the strap body, with a front surface, with a rear surface opposing the front surface of the at least one raised section, defining at least one channel spanning in a transverse direction and with at least one metallic weight disposed and retained therein, and defining an aperture spatially coupled to the at least one channel, the at least one metallic weight operably configured to be selectively and removably retained within the at least one channel of the at least one raised section;
a sanitizing raised section disposed transversely along the strap length, with an upper surface at least partially defining the upper surface of the strap body and defining an access aperture, with a front surface defining an aperture, with a rear surface opposing the front surface of the sanitizing raised section, and defining at least one channel spanning in a transverse direction and spatially connected to the access aperture and the aperture defined by front surface of the sanitizing raised section; and
a flexible sanitizing container disposed within the at least one channel defined by the sanitizing raised section and including a nozzle projecting outwardly from the aperture defined by front surface of the sanitizing raised section, the flexible sanitizing container operably configured to be accessible through the access aperture and flexed to cause emission of a sanitizing liquid configured to be housed in the flexible sanitizing container through the nozzle.

2. The sanitizing weighted bracelet according to claim 1, further comprising:
a housing structure of a substantially rigid material, disposed within the at least one channel defined by the sanitizing raised section, defining a housing cavity with the flexible sanitizing container disposed therein, having an upper housing surface defining a depression aperture spatially coupled to and disposed in an overlapping configuration with the access aperture, the flexible sanitizing container operably configured to be accessible through the access aperture and the depression aperture.

3. The sanitizing weighted bracelet according to claim 2, wherein:
the access aperture is enclosed by the upper surface of the sanitizing raised section and the depression aperture is enclosed by the upper housing surface of the housing structure.

4. The sanitizing weighted bracelet according to claim 2, wherein the housing structure further comprises:
a front surface defining a housing side aperture thereon and a rear surface opposing the front surface of the housing structure, the housing side aperture spatially coupled to and disposed in an overlapping configuration with the aperture defined by the front surface of the sanitizing raised section and with the nozzle projecting outwardly therefrom.

5. The sanitizing weighted bracelet according to claim 4, wherein the housing structure further comprises:
an upper shell and a lower shell selectively removably coupled together to collectively define the housing side aperture.

6. The sanitizing weighted bracelet according to claim 2, wherein:
the housing structure is compressively retained by the sanitizing raised section.

7. The sanitizing weighted bracelet according to claim 2, further comprising:
a one-way valve fluidly coupled to the flexible sanitizing container and the nozzle and operably configured to limit emission of the sanitizing liquid configured to be housed in the flexible sanitizing container in one direction through the nozzle.

8. The sanitizing weighted bracelet according to claim 1, wherein:
the raised section is disposed adjacent to the at least one raised section.

9. The sanitizing weighted bracelet according to claim 1, further comprising:
a plurality of raised sections each disposed transversely along the strap length and each defining at least one channel spanning in a transverse direction and with at least one metallic weight disposed and retained therein, the raised section is disposed adjacent to at least one of the plurality of raised sections.

10. The sanitizing weighted bracelet according to claim 9, wherein each of the plurality of raised sections further comprise:
a top surface at least partially defining the upper surface of the strap body, at least one perpendicular sidewall extending in a direction substantially perpendicular to the top surface, a front surface defining a front face aperture, a rear surface opposing the front surface, and a section width separating the rear surface and the front surface; and
a discontinuous upper slit defined by the at least one perpendicular sidewall of each of the plurality of raised sections flanking the upper slit, the upper slit spanning the section width of each the plurality raised sections defining the upper slit and terminating into a valley that at least partially defines the upper surface of the strap body.

11. The sanitizing weighted bracelet according to claim 1, wherein:
the aperture defined by the at least one raised section is defined by the front surface thereof, the at least one raised section defining two independent channels therein, spanning in a transverse direction, and with a metallic weight disposed and retained therein, each of the apertures defined by the front surface of the at least one raised section providing access to the two independent channels.

12. The sanitizing weighted bracelet according to claim 1, wherein:
the nozzle defines a distal tip defining an aperture offset a distance from the front surface of the sanitizing raised section and oriented at an acute angle α relative to a plane defined by the front surface of the sanitizing raised section.

13. The sanitizing weighted bracelet according to claim 1, further comprising:
a fastener disposed proximal to a first end defined by the strap body and a retention portion spanning from a second end defined by the strap body, terminating along a strap length separating the first and second ends of the strap body, and defining a plurality of retention apertures thereon, the fastener operably configured to be inserted through one of the plurality of retention apertures to form an enclosed and locked strap configured to surround the user's limb.

14. A sanitizing weighted bracelet comprising:
a strap body operably configured to define an enclosure to surround a user's limb, defining a longitudinal strap length, having an upper surface, and having a bottom surface opposing the upper surface of the strap body;
at least one raised section disposed transversely along the strap length, at least partially defining the upper surface of the strap body, with a front surface, with a rear surface opposing the front surface of the at least one raised section, defining at least one channel spanning in a transverse direction and with at least one metallic weight disposed and retained therein, and defining an aperture spatially coupled to the at least one channel, the at least one weight operably configured to be selectively and removably retained within the at least one channel of the at least one raised section;
a sanitizing raised section disposed transversely along the strap length, with an upper surface at least partially defining the upper surface of the strap body and defining an access aperture, with a front surface defining an aperture, with a rear surface opposing the front surface of the sanitizing raised section, and defining at least one channel spanning in a transverse direction and spatially connected to the access aperture and the aperture defined by front surface of the sanitizing raised section; and
a housing structure of a substantially rigid material, disposed within the at least one channel defined by the sanitizing raised section, defining a housing cavity, having an upper housing surface defining a depression aperture spatially coupled to and disposed in an overlapping configuration with the access aperture, the flexible sanitizing container operably configured to be accessible through the access aperture and the depression aperture a flexible sanitizing container disposed within the housing cavity and including a nozzle projecting outwardly from the aperture defined by front surface of the sanitizing raised section, the flexible sanitizing container operably configured to be accessible through the access aperture and the depression aperture, and flexed to cause emission of a sanitizing liquid configured to be housed in the flexible sanitizing container through the nozzle.

15. The sanitizing weighted bracelet according to claim 14, wherein:

the access aperture is enclosed by the upper surface of the sanitizing raised section and the depression aperture is enclosed by the upper housing surface of the housing structure.

16. The sanitizing weighted bracelet according to claim 14, wherein the housing structure further comprises:

a front surface defining a housing side aperture thereon and a rear surface opposing the front surface of the housing structure, the housing side aperture spatially coupled to and disposed in an overlapping configuration with the aperture defined by the front surface of the sanitizing raised section and with the nozzle projecting outwardly therefrom.

17. The sanitizing weighted bracelet according to claim 16, wherein the housing structure further comprises:

an upper shell and a lower shell selectively removably coupled together to collectively define the housing side aperture.

\* \* \* \* \*